United States Patent [19]

Baessler

[11] Patent Number: 4,503,862

[45] Date of Patent: Mar. 12, 1985

[54] TELEMETRY SYSTEM FOR MONITORING HOSPITAL PATIENT TEMPERATURE

[75] Inventor: Lee R. Baessler, Costa Mesa, Calif.

[73] Assignee: Bronco Aleksich, Los Angeles, Calif.; Trustee for Grennamyer Trust I

[21] Appl. No.: 298,184

[22] Filed: Aug. 31, 1981

Related U.S. Application Data

[63] Continuation of Ser. No. 68,758, Aug. 23, 1979, Pat. No. 4,321,933.

[51] Int. Cl.³ ............................................. A61B 5/00
[52] U.S. Cl. ........................................ 128/736; 128/903
[58] Field of Search ................................ 128/736, 903

[56] References Cited

U.S. PATENT DOCUMENTS

| | | | |
|---|---|---|---|
| 3,253,588 | 5/1966 | Vuilleumier et al. | 128/903 |
| 3,621,290 | 11/1971 | Fryer | 128/903 |
| 3,921,621 | 11/1975 | Bressler | 128/903 |
| 4,090,504 | 5/1978 | Nathan | 128/736 |
| 4,121,574 | 10/1978 | Lester | 128/736 |

Primary Examiner—William E. Kamm
Attorney, Agent, or Firm—Charles H. Thomas

[57] ABSTRACT

Hospital patient temperatures are monitored by providing each patient with a battery powered transmitter containing a thermister and reference resistor which is positioned over the patient's carotid artery. A receiver, carried by a nurse, includes an actuator for closing a reed switch in a transmitter near which it is positioned to activate that transmitter. Upon actuation of the transmitter, the patient's temperature varies the duty cycle of a high frequency transmitter output. The outputs of a number of transmitters, each associated with a different patient are elicited, one by one, and monitored by the receiver which contains a demodulator connected to a microprocessor coupled to a visual display. The microprocessor calculates patient temperature selectivily in Fahrenheit and Centigrade conventions. The microprocessor also detects low battery condition in the transmitter. The receiver includes a self-calibration test and low battery indication circuits.

3 Claims, 9 Drawing Figures

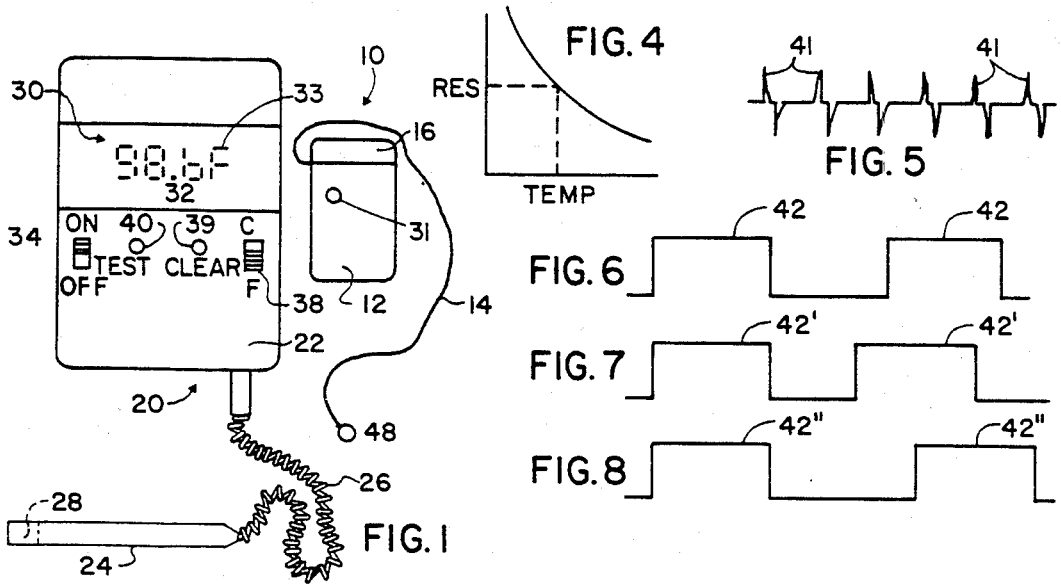
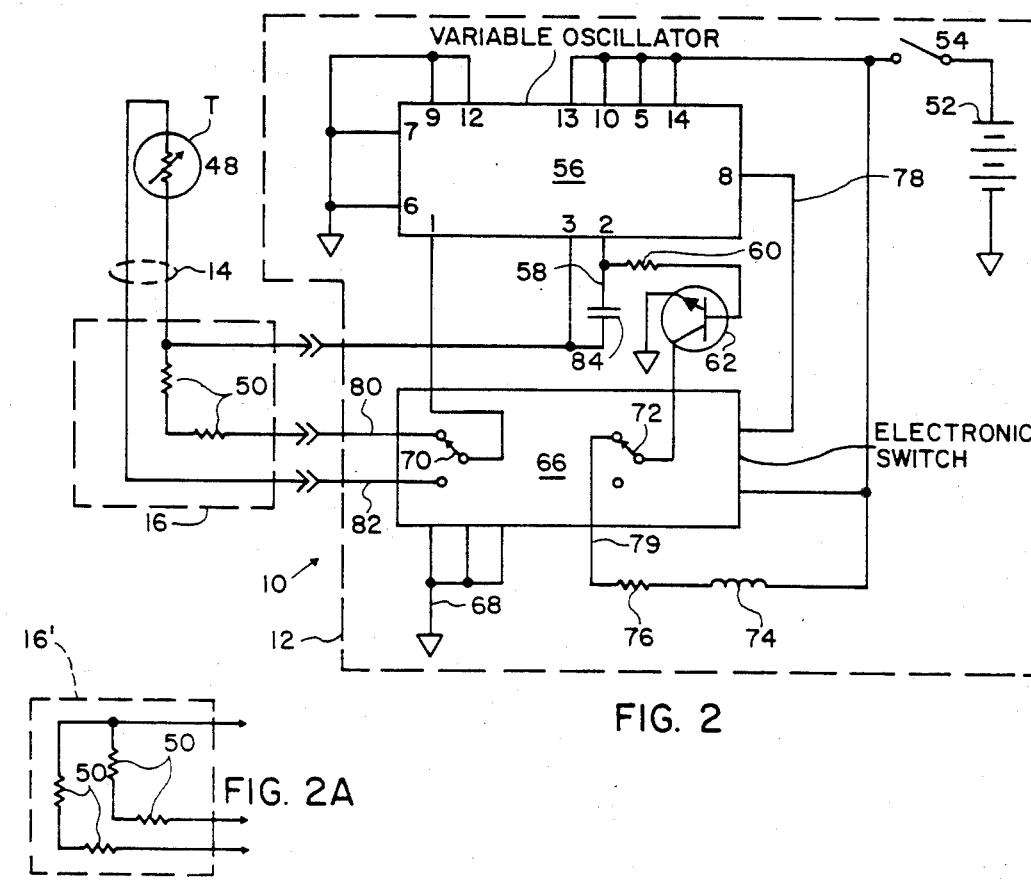

4,503,862

TELEMETRY SYSTEM FOR MONITORING HOSPITAL PATIENT TEMPERATURE

This is a continuation of application Ser. No. 68,758, filed Aug. 23, 1979, now U.S. Pat. No. 4,321,933 issued on Mar. 30, 1982.

BACKGROUND OF THE INVENTION

1. Field of the Invention

The present invention relates to devices for monitoring patient temperature in a hospital environment.

2. Description of the Prior Art

U.S. Pat. No. 3,921,621 discloses a patient temperature monitoring system which utilized discrete integrated circuit and analog components. Devices constructed according to that patent reduced considerably the time necessary for hospital nurses to monitor and record the temperatures of patients in their wards. However, the present invention has several features not found in prior patient temperature monitoring systems.

One object of the present invention is to provide a patient temperature monitoring system which can calculate and selectively display patient temperatures in either a Fahrenheit or Centigrade convention.

Another object of the invention is to provide a patient temperature monitoring system in which only one transmitter at a time is actuated. This is achieved by equipping the receiver, which is a portable unit carried by a nurse, with an antenna having an actuator affixed to the antenna. The actuator is merely brought into proximity of the transmitter associated with the patient whose temperature is to be monitored. The actuator closes a switch within the transmitter to provide power to the transmitter output unit. In the absence such switch closure, the switch is normally open and there is no power drain upon the transmitter batteries. Conventional mercury batteries are thereby able to last for years within each transmitter, and do not require recharging or replacement at approximately monthly intervals as do batteries associated with conventional patient temperature telemetry transmitting units.

A further object of the invention is to provide the receiver with a means for ascertaining when the transmitting battery voltage level has dropped to a point where further reduced voltage output will impair operation of the system. This is achieved in the present invention by a comparison function which compares a stored maximum reference duty cycle length with the duration of the reference duty cycle of the transmitter output measured during a test procedure. As the battery voltage level in the transmitter drops over a period of time, the duration of the reference duty cycle of the transmitter output attributable to the reference resistance will increase, even though the duration of thermistor portion will vary in accordance with patient temperature. When the total duration of the reference duty cycle of the transmitter increases to a maximum limit, the user of the receiver is informed that the transmitter battery level is low.

Another object of the invention is to provide a means for self-calibration of the receiver. The receiver includes a test circuit which is operated by a manual switch. Actuation of this switch to the test mode substitutes an internal reference oscillator output for the transmitter output. The internal reference oscillator is set to a predetermined duty cycle to produce a specific temperature indication in the display, such as 98.6° F. Deviation from this predetermined temperature indication informs the user that the instrument is out of calibration.

Yet a further object of the invention is to provide a transmitter for each patient in which the thermistor and reference resistor are encompassed together within a disposable packet. The packet is plug-in module and may be easily disconnected from the transmitter case. This avoids the necessity for sanitizing the packet containing the thermal resistor and thermistor elements, and instead allows these expendable components to be discarded and replaced with an identical, modular unit.

SUMMARY OF THE INVENTION

The present invention is a patient monitoring system which employs a plurality of transmitters, one associated with each patient to be monitored in a hospital ward. The temperature monitoring system includes a single portable receiver. Each transmitter is electrically powered and includes a plug-in packet containing a reference resistor pair and a thermistor which is located in thermal contact with a portion of the body of a patient where temperature is to be measured. Typically, the thermistor is applied to the patient over the carotid artery using a thermally insulating adhesive patch.

Each transmitter provides a high frequency output signal having a duty cycle proportional to a ratio of the value of resistance of the thermistor relative to the reference resistance. The receiver includes a demodulator responsive to the high frequency transmitter output signal providing an envelope signal of duration proportional to the duration of the transmitter duty cycle output. The receiver also includes a microprocessor which is coupled to receive an input from the demodulator and which is adapted to calculate patient temperature in both Fahrenheit and Centigrade conventions. The receiver also includes a visual display coupled to the microprocessor and including a manually actuable selector to alternatively display patient temperature in degrees Fahrenheit or in degrees Centigrade, and to indicate the convention selected.

DESCRIPTION OF THE DRAWINGS

FIG. 1 is depictes a physical embodiment of a receiver and a single transmitter of the invention.

FIG. 2 is a schematic diagram of a transmitter of the invention.

FIG. 2A is a schematic diagram of the resistor package according to the invention.

FIG. 4 is a graph illustrating the relationship between thermistor resistance and temperature.

FIG. 5 illustrates the pulse form of the transmitter output.

FIG. 6 illustrates pulse forms in the receiver demodulator for a normal patient temperature.

FIG. 7 illustrates pulse forms in the receiver demodulator for an abnormally high patient temperature.

FIG. 8 illustrates pulse forms in the receiver demodulator for an abnormally low patient temperature.

DESCRIPTION OF THE EMBODIMENT

Figure 3:
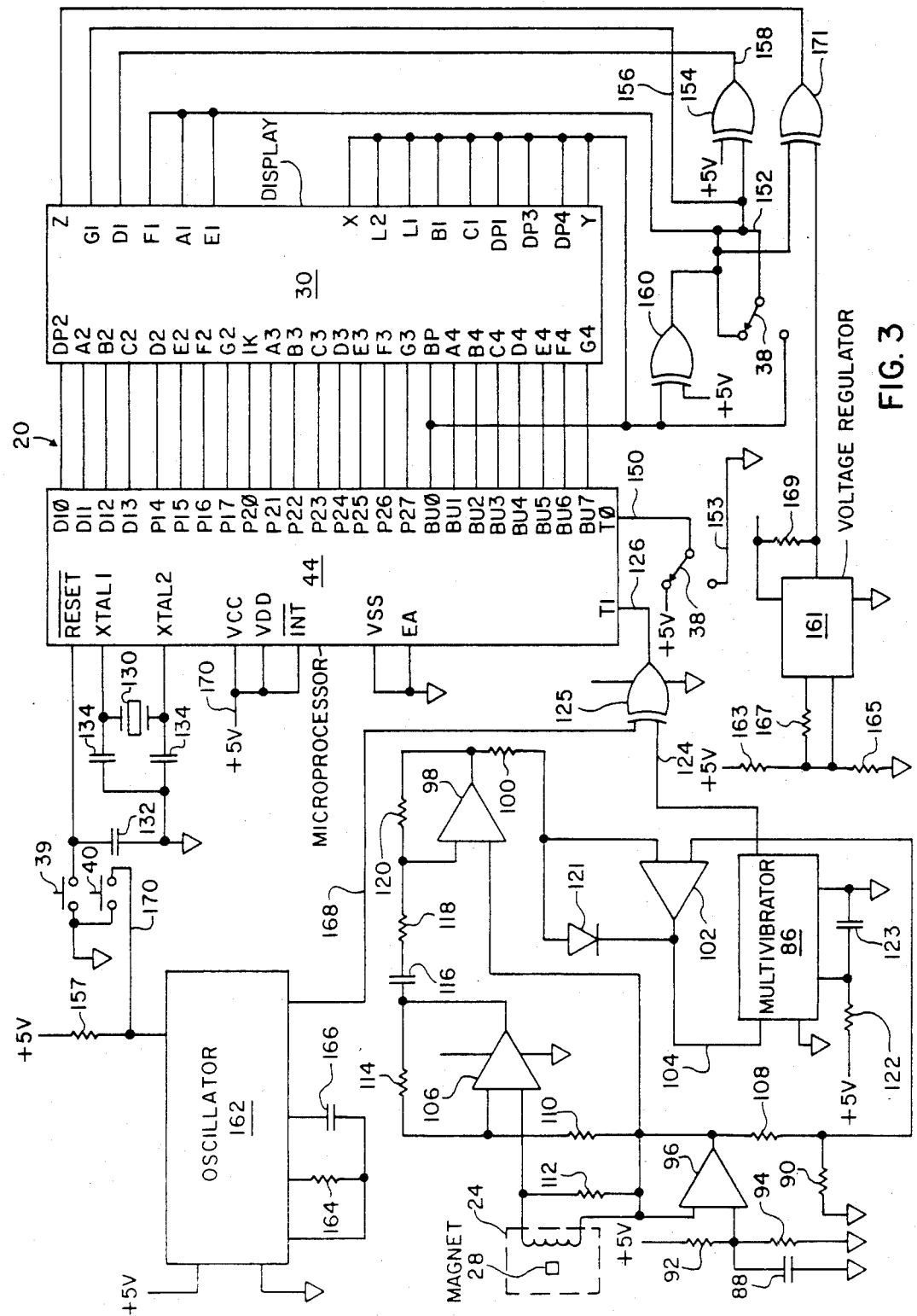
FIG. 3 is a schematic diagram of a receiver according to the invention.

FIG. 1 illustrates a patient temperature monitoring system for use in a hospital which includes a plurality of transmitters indicated generally at 10 and a single receiver 20. Each of the transmitters 10 is associated with a single patient to be monitored and includes a battery and a high frequency output signal generator housed within a generally rectangular, rigid walled case 12, for positioning on the patient whose temperature is to be monitored. At one end of the case 12 there is a disposable plug 16 which encompasses a reference resistor pair 50 and a thermistor mounted on the ends of electrical leads 14.

The receiver 20 is housed within a portable generally oblong rectangular case 22 to which an antenna wand 24 is attached by means of a coiled cable 26. Within the tip of the wand 24 there is an actuating magnet 28. In the case 22 the receiver 20 includes a visual display 30 that features 4½ digit positions and a decimal position 32 located to the left of the least significant digit position. The receiver 20 also includes an off/on slide switch 34, and a slide switch 38 for selection of Fahrenheit or Centigrade temperature conventions. In the case 22 the receiver 20 also has a switch 30 for clearing and resetting the system and a test switch 40 for use in checking calibration of the receiver 20.

The case 22 of the receiver 20 houses a demodulator responsive to the high frequency transmitter output signal from the transmitter 10. The wave form of the high frequency transmitter signal 10 is depicted in FIG. 5 and is generally in the frequency area of 20,000 kilocycles. The pulses of the output are denoted by the reference numeral 41. The demodulator of the receiver 20 responds to this signal to provide an envelope signal, indicated at 42 in FIG. 6, and transmits the squarewave pulse 42 to a microprocessor within the case 22, indicated at 44 in FIG. 3. The microprocessor 44 is preferably a model 8748 microprocessor manufactured and marketed by Intel Corporation of 3065 Bowers Ave., Santa Clara, Calif. 95001. The display 30 is a model FE 0206 liquid crystal display, manufactured by AND Incorporated, located in Burlingame, Calif.

In FIG. 2 the thermistor of the transmitter 10 is depicted at 48, and the reference resistor pair is depicted at 50. The relationship between temperature and resistance of the thermistor 48 is illustrated graphically in FIG. 4. Resistance declines with increasing temperature, and in the preferred embodiment of the system, the relationship between temperature and resistance is set forth in Table I herebelow.

TABLE I

| °C. | °F. | Resistance (ohms) |
|---|---|---|
| 35 | 95.0 | 65.8K |
| 36 | 96.8 | 63.2K |
| 37 | 98.6 | 60.7K |
| 38 | 100.4 | 58.3K |
| 39 | 102.2 | 56.0K |
| 40 | 104.0 | 53.8K |
| 41 | 105.8 | 51.7K |
| 42 | 107.6 | 49.7K |
| 43 | 109.4 | 47.8K |
| 44 | 111.2 | 46.0K |
| 45 | 113.0 | 44.3K |

The resistance of the reference resistor pair 50 in ohms is preferably equal to the 98.6° F. value of the thermistor. Accordingly, the resistance value of the reference resistor pair 50 is selected to correspond to a temperature of 98.6° F. or 37.0° C., which is, in the preferred embodiment, a resistance of 60,700 ohms.

With the foregoing temperature/resistance relationship in mind, and with the preferred embodiment of the invention, the thermistor 48 and the reference resistor pair 50 are alternatively switched into the transmitter circuit. With this arrangement patient temperature can be calculated quite closely from the following algorithm.

$$T = K1 + \frac{(R_r - R_t)}{(R_r + R_t)} \times K2$$

In the above algorithm $R_r$ is equal to the resistance of the reference resistor pair 50 while $R_t$ is equal to the resistance of the thermistor 48. T is temperature and K1 and K2 are constants. With the embodiment of the invention depicted, for temperatures in the Fahrenheit convention, the constant K1 is equal to 98.6 and the constant K2 is equal to 90.0. Temperatures in the centigrade convention can be determined from the conventional algorithm $C=(5/9)(F-32)$.

The electrical components of the patient monitoring device are depicted schematically in FIGS. 2 and 3. The transmitter 10 is illustrated in FIG. 2. The transmitter 10 is powered by a 7.0 volt mercury battery 52 having a negative terminal connected to common and the positive terminal connected through a reed switch 54. The read switch 54 is actuated by the magnet 28 on the antenna wand 24 as will hereinafter be described. The read switch 54 is connected to a variable oscillator 56, which is a single chip, solid state device having an oscillator with a built in divider. The variable oscillator 56 is preferably a model 14541B Variable Oscillator, manufactured by Motorola Corporation. The variable oscillator 56 produces a high frequency output signal on line 58. The frequency of the output on the line 58 is approximately 20 kilohertz. Line 58 connected to a resistor 60, which may be 33K ohms. The resistor 60 is connected to the base of an output transistor 62 which provides a high frequency output at its collector.

The transmitter 10 also includes within its housing case 22 an electronic switch 66. Preferably, the electronic switch 66 may be purchased as a two poles, four position switch, model number 14052 from Motorola Corporation. One of the sides of one of the switch controls is connected to common at 68, so that the switch 66 is utilized as single chip, double pole, double throw solid state electronic switch including tandem operated switches 70 and 72. The electronic switch 66 is powered by the battery power supply 52. Control of the alternative positions of the switches 70 and 72 is effectuated though a divided down output from the variable oscillator 56 on line 78. The output on line 78 is a low frequency output with an output period proportional to and at least 100 times the output period of the high frequency output on line 58. Preferably, the frequency of the output on line 78 is equal to the frequency output on line 58 divided by 1024.

The switch contact 72 of the electronic switch 66 may be moved alternatively between an open position and a connection to line 79, which in turn is connected to the battery power supply 52 through a 1.0 K ohm resistor 76 and 82 microhenry inductor 74 when the read switch 54 is closed. The switch contact 72 is coupled continuously to the collector of the RF output transistor 62. When the switch contact 72 of the electronic switch 66 is coupled to line 79, as depicted in FIG. 2, collector current is supplied and the high frequency output transistor 62 transmits high frequency pulses of the wave form depicted in FIG. 5 of approximately 20 kilohertz. When the switch contact 72 is in the position opposite that depicted in FIG. 2, no collector current is supplied to the transistor 62 so that there is no high frequency output.

The other switch contact 70 in the electronic switch 66 is connected to the variable oscillator 56 continuously, and alternatively either to line 80 leading to the reference resistor pair 50, or to line 82 leading to the thermistor 48. When the switch contact 70 is in the position depicted in FIG. 2, the reference resistor pair 50 is connected across pins 1 and 3 of the variable oscillator 56. A 560 picofarad capacitor 84 is coupled in circuit in line 58. The value of the resistance connected across pins 1 and 3 of the variable oscillator 56 and capacitor 84 govern the frequency of the output on line 58 to the transistor 62.

The switch contacts 70 and 72 are reversed with each cycle appearing on line 78. Since the signal on line 78 is divided down by 1024 from the frequency appearing on line 58, that number of pulses will be transmitted on line 58 for each pulse appearing on line 78.

When the switch contacts 70 and 72 are in the position depicted in FIG. 2, the refence resistor pair 50 is connected across pins 1 and 3 of the variable oscillator 56 and collector current is conducted on line 79 to the transistor 62 to generate a high frequency output on line 79. This output is transmitted to the receiver 20 until occurrence of the next sequential pulse on the divided down output line 78, whereupon switch contacts 70 and 72 are reversed from the positions depicted. While in the reversed positions, signals still appear on line 58 with a period proportional to the resistance value of the thermistor 48. However, there is no output from the RF transistor 62 since the switch contact 72 is open. With the following sequential pulse on the divided down output line 78, the switch contacts 70 and 72 are again reversed and the transistor 62 again generates high frequency output pulses.

The transmitter 10 is calibrated so that the duty cycle of the transmission of pulses from transistor 62 is equal to the reference interval of the transmission periods. For this reason, the reference resistor pair 50 is selected and the system is conditioned so that if the temperature sensed by the thermistor 48 is normal human body temperature (98.6° F., 37° C.), the transistor 62 will generate RF output pulses exactly half of the time. The waveform of output of the transistor 62 will then be as depicted in FIG. 6. If, on the other hand, patient temperature is above normal, the resistance of the thermistor 48 will be reduced, and the corresponding period of time during which the transistor 62 does not conduct will be shortened. Correspondingly, the conductive or reference portion of the transmitter output waveform will remain constant as illustrated in FIG. 7. When the opposite condition exists and the patient temperature is below normal, as indicated by the thermistor 48, the portion of the overall cycle of operation during which transistor 62 does not conduct will be increased. This will increase the duty cycle of the output of transistor 62, as illustrated in FIG. 8.

The electrical components of the receiver 20 are depicted in FIG. 3. The receiver 20 employs a microprocessor 44 which performs all of the calculating and display control functions required. The receiver 20 includes as a demodulator a retriggerable monostable multivibrator 86. When the antenna in the wand 24 is positioned to activate the transmitter 10, the RF signal from the transmitter transistor 62 is received and acts upon a 2.7 K ohm resistor 112. The five volt power supply from the receiver battery acts across a voltage divider having a 6.8 K ohm resistor 92 and 3 K ohm resistor 94. A 22 microfarad capacitor 88 is coupled from the resistor junction to ground.

The voltage dividing network is coupled as one input to a quad operational amplifier system. The amplifier 96 receives a signal from the junction of the resistors 92 and 94 which represents a reference voltage in the system. The high frequency input signal received across resistor 112 is amplified by the network composed of amplifiers 106 and 98, resistors 110, 114, 118, 120 and capacitor 16. The input and feedback resistors of these inverting amplifiers are selected to give a total gain of 300.

Resistors 90 and 108 make up a voltage divider that produces a voltage 0.3 volts less than the reference voltage. This voltage and the output of amplifier 98 are applied to the inputs of amplifier 102 which acts as a level detector. When the amplified high frequency signal exceeds 0.3 volts the output of amplifier 102 is caused to change state. Resistor 100 and diode 121 act to keep amplifier 102 out if saturation thereby allowing it to respond quickly to the amplified high frequency signal. The output of amplifier 102 is applied to the input of retriggerable one shot monostable multivibrator 86.

The demodulator of the receiver 20 is a retriggerable one shot monostable multivibrator, model 4538 manufactured and sold by Motorola Company. The five volt d.c. receiver power supply is connected through a 33 to 47 K ohm resistor 122 and a 0.0022 microfarad capacitor 123 to the multivibrator 86. The multivibrator 86 emits a pulse which lasts for a selected duration of perhaps 85 microseconds. If retriggered once the pulse is initated, the duration of the output pulse of the multivibrator 86 will be extended in duration accordingly. During measurement of patient temperature, the reference resistor pair 50 in the transmitter 10 creates a train of pulses, indicated in FIG. 5. The positive going edges of these pulses occur at approximately 50 microsecond intervals. These pulses repeatedly retrigger the multivibrator 86 as long as they continue to occur. Accordingly, the multivibrator 86 will generate an envelope signal on line 124 to the microprocessor 44 through the exclusive OR gate 125.

The retriggerable one shot multivibrator 86 will remain conductive until high frequency pulses are no longer detected, since each sequential high frequency pulse will retrigger multivibrator 86 and extend the duration of the envelope signal output thereof. This output is of the type and configuration described in conjunction with FIGS. 6–8. The duration of the envelope signal to the microprocessor 44 is essentially equal to the duration of the duty cycle of the high frequency output signal on line 79 from the transmitter 10. In this fashion, the monostable multivibrator 86 passes an envelope signal to the microprocessor 44 at an input on line 126. The use of the retriggerable monostable multivibrator 86 ensures a clean, squarewave envelope signal of duration closely proportional to the duty cycle of the output of the transmitter 10. If conventional capacitive type filters where employed to generate the envelope signal, considerable ringing would occur, and extra pulses would be generated. This would distort the envelope signal so that it would no longer be closely proportional to the duty cycle of the transmitter output.

A crystal 130 is coupled to the microprocessor 44 as indicated in FIG. 3 in circuit with a one microfarad capacitor 132, and 20 picofarad capacitors 134. The crystal 130 regulates a high frequency signal in the microprocessor 44. The microprocessor 44 utilizes an area of its ram memory for storage and directs counts derived from the crystal 130 into this memory storage location. This ram memory location accumulates counts proportional to the reference phase and thermistor phase of the transmitted high frequency signal. These counts are then used in the algorithm programmed into the microprocessor.

The temperature convention selection switch 38 is connected by line 150 to input T0 of the microprocessor 44. This convention selection switch determines which of the stored Fahrenheit or Centrigrade temperatures is to be displayed. The switch 38 may be connected either to the 5 volt receiver power supply when temperature is to be displayed in degrees Fahrenheit, or to ground at line 153 if temperature is to be displayed in the Centigrade convention. The switch 38 is also connected as a gate to line 152 which is coupled to an exclusive OR gate 154 and to line 156. The output of exclusive OR gate 154 is on the line 158. Together the lines 156 and 158 control the segments of the last digit position in the display 30 to display either a "C" or "F" depending upon whether the Centigrade or Fahrenheit convention has been selected. Lines 156 and 158 control illumination of the two segments of the seven segment display which are different as between a "C" and an "F". The signal provided to switch 38 for this purpose from the microprocessor 44 is from pin BU0, the output of which is passed through an exclusive OR gate 160 for the Fahrenheit convention selection signal. The receiver battery is connected to a voltage regulator 161 through a voltage divider network including resistors 163, 165 and 167. The output of the voltage regulator 161 is stabilized by a pull-up resistor 169 and directed through an exclusive OR gate 171 to the "LO BAT" symbol on the liquid crystal display 30.

The receiver 20 also includes an internal CMOS oscillator 162 which is preferably the same model of variable oscillator employed as oscillator 56 in the transmitter 10. The oscillator 162 is powered from the 5 volt receiver power supply and includes a fixed resistor 164, preferably of 56 K ohms, and a fixed capacitor 166, preferably having a value of 510 picofarads. This causes the oscillator 162 to produce a divided down output on line 168 corresponding to the output on line 78 in the transmitter 10, but controlled to represent precisely a known temperature, preferably the normal human body temperature of 98.6° F. or 37.0° C.

With the test push botton switch contact 40 moved to establish a circuit to line 170, the oscillator 162 is turned on to provide a reference high frequency output signal on line 168 to the microprocessor 44. The exclusive OR gate 126 allows reception of signals from the oscillator 162 or from the transmitter 10. Upon receipt of the reference high frequency output signal on line 168 at pin T1, the microprocessor operates upon that signal to calculate temperature, the same as it does for signals reeived from the transmitter 10. The microprocessor 44 thereby produces an image of temperature in the display 30. The temperature produced may be visually compared against a known temperature associated with the internal oscillator 162. Because the normal human body temperature is an easy reference for hospital personnel, this is preferably the temperature to which the resistor 164 and capacitor 166 are calibrated. Any deviation from this temperature appearing in the display 30 when the switch 40 is in the test mode signals to the operator a malfunction in the receiver 20.

The transmitter 10 also is adapted to accomodate a resistor package in place of the plug 16 bearing the thermistor 48 and reference resistor 50. Such a reference resistor package is visually similar to the plug 16, and is schematically illustrated at 16' in FIG. 2A. However, the reference resistor package contains two pairs of reference resistors 50, one of the pairs of which replaces the thermistor 48. When this references resistor package is coupled in plug in fashion to the case 12, the microprocessor 44 can detect a standardized duration of the envelope signal cycle. Since the two resistors 50 that are alternatively connected to the variable oscillator 56 are equal, the duration of the envelope signal will be exactly one-half the total cyclic period between leading edges of sequential envelope signals, and will not vary except in response to declining voltage of the battery 52 in the transmitter 10. Accordingly, the microprocessor 44 contains in memory a number corresponding to a maximum envelope signal duration which is inversely proportional to a minimum acceptable voltage of the transmitter battery 52. By comparing the envelope signal received at pin T1 with the stored maximum envelope signal duration, the microprocessor 44 is able to provide a signal indication in the display 30 when the voltage of the battery 52 becomes inadequate. The operator is thereby able to test the transmitter batteries of the various transmitter units as desired, and to replace those transmitter units in which the voltage level is inadequate.

The operator is also informed of the battery condition of the receiver 20. The microprocessor 44 will operate on a d.c. voltage of from between 5.5 and 4.5 volts. The receiver battery is connected directly to the microprocessor 44 by line 170. The level detector 161 compares the voltage level detected from the receiver battery with the voltage produced by the voltage divider made up of resistors 163, 165, 167 of 4.75 volts. Whenever the receiver battery level drops below 4.75 volts, the level detector 161 operates the display 30 to signal a low voltage power condition in the battery. This signal appears on the display 30 as a message "LO BAT". The nurse operating the receiver is thereby informed that the receiver must be recharged within about an hour of further continuous use.

The microprocessor 44 is programmed as indicated in the program listing, attached as Appendix A hereto. In the program sequence of Appendix A, the program initially jumps over the timer interrupt steps at sequence step 13 and tests for a true or high condition of input T1 of the microprocessor 44 connected to line 126. This test occurs at sequence step 23. If an envelope signal is present on line 126, T1 will be true and the microprocessor 44 is then put into a delay routine whereby it delays processing of the envelope signal to ensure that the envelope signal continues to appear on line 126 in a consistent, recurring fashion. The delay routine appears from steps 23 through 31. At sequence step 32 the microprocessor 44 activates the decimal point location 32 in the display 30 by an output on pin P10. Illumination of the decimal point position 32 indicates to the nurse using the temperature monitoring system receipt of the temperature information from the transmitter 10 by the receiver 20. A further delay of one cycle occurs at steps 34 through 37.

Once the delay interval has elapsed, the microprocessor accumulates counts proportional to the reference phase of the transmitted signal. This occurs from steps 38 through 58. The microprocessor then accumulates counts proportional to the thermistor phase of the transmitted signal. This occurs at steps 62 through 82. The system thereupon jumps to error detection routine at sequence step 85 of Appendix A. This routine tests the number stored during the reference phase of the envelope signal against maximum and minimum numbers corresponding to maximum and minimum allowed count. If the number accumulated during the reference phase of the envelope signal on line 126 falls beyond the prescribed maximum and minimum limits, the system branches to an error display routine. If the count is within limits, however, the microprocessor 44 branches to sequence step 99 of Appendix A.

The system then proceeds to perform arithmetic operations which ultimately calculate patient temperature in degrees Fahrenheit, and subsequently in degrees Centigrade. This routine is initiated at sequence step 99 at page 2 of Appendix A where the reference and thermistor resistance values are called from storage and added together. This sum is stored at program sequence step 118 of Appendix A. The system then jumps to sequence step 172 where it clears out a temporary memory storage location where the results of the arithmetic operations are to be maintained. The constant K2 is then applied to the algorithm hereinbefore described for computing Fahrenheit temperature at sequence step 178 of Appendix A. The arithmetic steps to compute temperature in degrees Fahrenheit and in degrees centigrade are thereafter performed in the sequence steps Appendix A. If the Fahrenheit temperature calculated is greater than 129.9 degrees or less than 40.0 degrees, the microprocessor 44 will produce an error message ERR on the display 30 at sequence steps 360 through 372 of Appendix A. Between sequency steps 290–346 of Appendix A a correction in the algorithm is performed to improve the accuracy of temperature indications below 95° F. If no error condition is detected, the microprocessor 44, after storing the Fahrenheit temperature, proceeds to calculate temperature in degrees Centigrade. This conversion is carried out from sequence step 373 to about sequence step 405 Appendix A.

After computation and storage of the Fahrenheit and Centigrade temperatures, the microprocessor 44 then keeps examining the temperature convention to be displayed and sequences through the phases on the liquid crystal display to operate the display 30 properly. The seven segments of the display 30 are decoded and stored in ram memory so that the microprocessor 44 can look at a stored temperature number and can make the conversion to activate the appropriate pins of the display 30. The microprocessor program generation of the error code to the segment display begins in the subroutine commencing at sequence step 426 of Appendix A. The display subroutine itself commences at subsequent step 598 of Appendix A.

To use the patient temperature monitoring system of the invention, the temperature transmitter case 12 and the plug 16 containing the reference resistor pair 50 is positioned in the vicinity of the patient and the thermister 48 is placed over the patient's corotid artery. A nurse carrying the receiver 20 with the case 22 in one hand and the wand 24 in the other can sequentially and rapidly monitor and record patient temperatures, moving from one patient to the next very quickly. The nurse positions the extremity of the wand 24 bearing the magnet 28 proximate to a marked position 31 on the transmitter case 22. The reed switch 54 (FIG. 2) is located immediately beneath the surface of the case at the position 31 so that the magnet 28 closes the reed switch 54 and allows the transmitter battery 52 to supply power to the oscillator 56. This activates the high frequency output transistor 62 to generate the high frequency signal of FIG. 5. The antenna in the wand 24 detects this high frequency output signal and the receiver 20 demodulates it in the retriggerable monostable multivibrator 86. The microprocessor 44 converts the duration of the envelope signal appearing at pin T1 to a temperature in either degrees Centigrade or degrees Fahrenheit, as selected by the temperatre selection switch 38 in the receiver 20.

Immediately upon detecting the envelope signal on line 126, the microprocessor 44 displays the decimal point 32 in the display 30, although it allows the transmitter 10 to stabilize for another cycle of the envelope signal before measuring the envelope signal duration and calculating temperature. Upon doing so, temperature appears in the display 30, along with an indication of the temperatuure convention selected, "C" or "F", at the digit position 33 in the display 30. If the envelope signal indicates a temperature out of limits of the range of acceptable temperatures or the battery voltage of the transmitter is too low, an error signal "ERR" will appear in the display 30. If an acceptable temperature is received, the nurse will record the temperature appearing in the display 30 in association with the hospital records of the patient concerned. The nurse will then depress the switch 39 to clear the microprocessor or in preparation for temperature measurement of the next patient.

Because the reference resistor pair 50 and thermistor 48 are alternatively coupled into the same transmitter circuitry, any aging of the circuit components or other influences upon the circuitry will effect both the thermistor 48 and the reference resistor 50 equally. As a consequence, the envelope signal produced is an extremely accurate indication of actual patient temperature.

Undoubtedly numerous variations and modifications of the invention will become readily apparent to those skilled in the art. Accordingly, the scope of the invention should not be construed as limited to the specific embodiment depicted, but rather is defined in the claims appended hereto.

| ASM48 ATHRML.ASM DEBUG | | | |
|---|---|---|---|
| ISIS-II MCS-48/UPI-41 MACRO ASSEMBLER, V2.0 | | | |
| LOC | OBJ | SEQ | SOURCE |
| | | 1 | |
| | | 2 | |
| | | 3 | |
| | | 4 | |
| | | 5 | |
| 0000 | | 6 | ORG |
| 0000 | 0409 | 7 START: | JMP |

ASM48 ATHRML.ASM DEBUG
ISIS-II MCS-48/UPI-41 MACRO ASSEMBLER, V2.0

| | | | | |
|---|---|---|---|---|
| 0002 | 00 | 8 | | NOP |
| 0003 | 00 | 9 | | NOP |
| 0004 | 00 | 10 | | NOP |
| 0005 | 00 | 11 | | NOP |
| 0006 | 00 | 12 | | NOP |
| 0007 | 64A4 | 13 | GODISP: | JMP |
| 0009 | E5 | 14 | PROG: | SEL |
| 000A | C5 | 15 | | SEL |
| 000B | 27 | 16 | | CLR |
| 000C | 62 | 17 | | MOV |
| 000D | 25 | 18 | | EN |
| 000E | 55 | 19 | | STRT |
| 000F | B83F | 20 | | MOV |
| 0011 | A0 | 21 | PROG0: | MOV |
| 0012 | E811 | 22 | | DJNZ |
| 0014 | 5618 | 23 | REFPHX: | JT1 |
| 0016 | 0414 | 24 | | JMP |
| 0018 | 461F | 25 | REFPHY: | JNT1 |
| 001A | 0418 | 26 | | JMP |
| 001C | 00 | 27 | | NOP |
| 001D | 00 | 28 | | NOP |
| 001E | 00 | 29 | | NOP |
| 001F | 5623 | 30 | REFPH: | JT1 |
| 0021 | 041F | 31 | | JMP |
| 0023 | B83D | 32 | REFPH0: | MOV |
| 0025 | 10 | 33 | | INC |
| 0026 | 462A | 34 | REFPH4: | JNT1 |
| 0028 | 0426 | 35 | | JMP |
| 002A | 562E | 36 | REFPH1: | JT1 |
| 002C | 042A | 37 | | JMP |
| 002E | 35 | 38 | REFPH2: | DIS |
| 002F | 00 | 39 | | NOP |
| 0030 | 00 | 40 | | NOP |
| 0031 | 00 | 41 | | NOP |
| 0032 | 00 | 42 | | NOP |
| 0033 | B828 | 43 | | MOV |
| 0035 | B929 | 44 | | MOV |
| 0037 | BA01 | 45 | | MOV |
| 0039 | 27 | 46 | | CLR |
| 003A | A0 | 47 | | MOV |
| 003B | A1 | 48 | | MOV |
| 003C | 17 | 49 | | INC |
| 003D | 464C | 50 | REFPH3: | JNT1 |
| 003F | 6A | 51 | | ADD |
| 0040 | 57 | 52 | | DA |
| 0041 | E63D | 53 | | JNC |
| 0043 | 21 | 54 | | XCH |
| 0044 | 6A | 55 | | ADD |
| 0045 | 57 | 56 | | DA |
| 0046 | 21 | 57 | | XCH |
| 0047 | 043D | 58 | | JMP |
| 0049 | 00 | 59 | | NOP |
| 004A | 00 | 60 | | NOP |
| 004B | 00 | 61 | | NOP |
| 004C | 20 | 62 | TMPPH: | XCH |
| 004D | 27 | 63 | | CLR |
| 004E | B82A | 64 | | MOV |
| 0050 | B92B | 65 | | MOV |
| 0052 | BA01 | 66 | | MOV |
| 0054 | A0 | 67 | | MOV |
| 0055 | A1 | 68 | | MOV |
| 0056 | 17 | 69 | | INC |
| 0057 | 00 | 70 | | NOP |
| 0058 | 00 | 71 | | NOP |
| 0059 | 00 | 72 | | NOP |
| 005A | 00 | 73 | | NOP |
| 005B | 5669 | 74 | TMPPH1: | JT1 |
| 005D | 6A | 75 | | ADD |
| 005E | 57 | 76 | | DA |
| 005F | E65B | 77 | | JNC |
| 0061 | 21 | 78 | | XCH |
| 0062 | 6A | 79 | | ADD |
| 0063 | 57 | 80 | | DA |
| 0064 | 21 | 81 | | XCH |
| 0065 | 045B | 82 | | JMP |
| 0067 | 00 | 83 | | NOP |
| 0068 | 00 | 84 | | NOP |
| 0069 | 20 | 85 | ERRDET: | XCH |
| 006A | 25 | 86 | ERR0: | EN |
| | | 87 | | ; |

-continued
ASM48 ATHRML.ASM DEBUG
ISIS-II MCS-48/UPI-41 MACRO ASSEMBLER, V2.0

|  |  |  |  |  |
|---|---|---|---|---|
|  |  | 88 |  | ; |
|  |  | 89 |  | ; |
| 006B | B829 | 90 |  | MOV |
| 006D | F0 | 91 |  | MOV |
| 006E | 03DC | 92 |  | ADD |
| 0070 | F679 | 93 |  | JC |
| 0072 | F0 | 94 |  | MOV |
| 0073 | 03EE | 95 |  | ADD |
| 0075 | E679 | 96 |  | JNC |
| 0077 | 047B | 97 |  | JMP |
| 0079 | 6400 | 98 | ERR1: | JMP |
| 007B | 00 | 99 | PROGRM: | NOP |
| 007C | 7414 | 100 |  | CALL |
| 007E | BA02 | 101 |  | MOV |
| 0080 | B828 | 102 |  | MOV |
| 0082 | B920 | 103 |  | MOV |
| 0084 | 749C | 104 | PROG1: | CALL |
| 0086 | EA84 | 105 |  | DJNZ |
| 0088 | BA02 | 106 |  | MOV |
| 008A | B82A | 107 |  | MOV |
| 008C | B924 | 108 |  | MOV |
| 008E | 749C | 109 | PROG2: | CALL |
| 0090 | EA8E | 110 |  | DJNZ |
| 0092 | 7488 | 111 |  | CALL |
| 0094 | BA04 | 112 |  | MOV |
| 0096 | B820 | 113 |  | MOV |
| 0098 | B924 | 114 |  | MOV |
| 009A | 749C | 115 | HAFRT: | CALL |
| 009C | EA9A | 116 |  | DJNZ |
| 009E | 74C2 | 117 |  | CALL |
| 00A0 | BA02 | 118 |  | MOV |
| 00A2 | B824 | 119 |  | MOV |
| 00A4 | B92C | 120 |  | MOV |
| 00A6 | 749C | 121 | PROG3: | CALL |
| 00A8 | EAA6 | 122 |  | DJNZ |
| 00AA | 7414 | 123 |  | CALL |
| 00AC | 00 | 124 |  | NOP |
| 00AD | 00 | 125 |  | NOP |
| 00AE | 00 | 126 |  | NOP |
| 00AF | 04EA | 127 |  | JMP |
| 00B1 | B93D | 128 | TMPSEL: | MOV |
| 00B3 | B83C | 129 |  | MOV |
| 00B5 | F0 | 130 |  | MOV |
| 00B6 | AA | 131 |  | MOV |
| 00B7 | 36D1 | 132 |  | JT0 |
| 00B9 | B836 | 133 |  | MOV |
| 00BB | F0 | 134 | TMP1: | MOV |
| 00BC | 03F0 | 135 |  | ADD |
| 00BE | E3 | 136 |  | MOVP3 |
| 00BF | A1 | 137 |  | MOV |
| 00C0 | 11 | 138 |  | INC |
| 00C1 | 18 | 139 |  | INC |
| 00C2 | 19 | 140 |  | INC |
| 00C3 | F0 | 141 |  | MOV |
| 00C4 | 03F0 | 142 |  | ADD |
| 00C6 | E3 | 143 |  | MOVP3 |
| 00C7 | A1 | 144 |  | MOV |
| 00C8 | 18 | 145 |  | INC |
| 00C9 | 19 | 146 |  | INC |
| 00CA | F0 | 147 |  | MOV |
| 00CB | 03F0 | 148 |  | ADD |
| 00CD | E3 | 149 |  | MOVP3 |
| 00CE | A1 | 150 |  | MOV |
| 00CF | 04B1 | 151 |  | JMP |
| 00D1 | B839 | 152 | TMP2: | MOV |
| 00D3 | F0 | 153 | TMP3: | MOV |
| 00D4 | 03F0 | 154 |  | ADD |
| 00D6 | E3 | 155 |  | MOVP3 |
| 00D7 | A1 | 156 |  | MOV |
| 00D8 | 11 | 157 |  | INC |
| 00D9 | 18 | 158 |  | INC |
| 00DA | 19 | 159 |  | INC |
| 00DB | F0 | 160 |  | MOV |
| 00DC | 03F0 | 161 |  | ADD |
| 00DE | E3 | 162 |  | MOVP3 |
| 00DF | 6A | 163 |  | ADD |
| 00E0 | A1 | 164 |  | MOV |
| 00E1 | 18 | 165 |  | INC |
| 00E2 | 19 | 166 |  | INC |
| 00E3 | F0 | 167 |  | MOV |

-continued
ASM48 ATHRML.ASM DEBUG
ISIS-II MCS-48/UPI-41 MACRO ASSEMBLER, V2.0

| | | | | |
|---|---|---|---|---|
| 00E4 | 03F0 | 168 | | ADD |
| 00E6 | E3 | 169 | | MOVP3 |
| 00E7 | A1 | 170 | | MOV |
| 00E8 | 04B1 | 171 | | JMP |
| 00EA | 27 | 172 | FTMP: | CLR |
| 00EB | BA08 | 173 | | MOV |
| 00ED | B82E | 174 | | MOV |
| 00EF | A0 | 175 | FPRG: | MOV |
| 00F0 | 18 | 176 | | INC |
| 00F1 | EAEF | 177 | | DJNZ |
| 00F3 | 7414 | 178 | | CALL |
| 00F5 | BA02 | 179 | | MOV |
| 00F7 | B828 | 180 | | MOV |
| 00F9 | B924 | 181 | | MOV |
| 00FB | 749C | 182 | PRGA: | CALL |
| 00FD | EAFB | 183 | | DJNZ |
| 00FF | 745C | 184 | | CALL |
| 0101 | BB67 | 185 | | MOV |
| 0103 | 741E | 186 | | CALL |
| 0105 | BA04 | 187 | | MOV |
| 0107 | B820 | 188 | | MOV |
| 0109 | B92E | 189 | | MOV |
| 010B | 749C | 190 | PRGB: | CALL |
| 010D | EA0B | 191 | | DJNZ |
| 010F | 7414 | 192 | | CALL |
| 0111 | BA02 | 193 | | MOV |
| 0113 | B82A | 194 | | MOV |
| 0115 | B924 | 195 | | MOV |
| 0117 | 749C | 196 | PRGC: | CALL |
| 0119 | EA17 | 197 | | DJNZ |
| 011B | 745C | 198 | | CALL |
| 011D | BB67 | 199 | | MOV |
| 011F | 741E | 200 | | CALL |
| 0121 | BA04 | 201 | | MOV |
| 0123 | B820 | 202 | | MOV |
| 0125 | B932 | 203 | | MOV |
| 0127 | 749C | 204 | PRGD: | CALL |
| 0129 | EA27 | 205 | | DJNZ |
| 012B | 7414 | 206 | PRGE: | CALL |
| 012D | BA04 | 207 | | MOV |
| 012F | B82E | 208 | | MOV |
| 0131 | B924 | 209 | | MOV |
| 0133 | 749C | 210 | PRGF: | CALL |
| 0135 | EA33 | 211 | | DJNZ |
| 0137 | BA02 | 212 | | MOV |
| 0139 | B82C | 213 | | MOV |
| 013B | B920 | 214 | | MOV |
| 013D | 749C | 215 | PRGG: | CALL |
| 013F | EA3D | 216 | | DJNZ |
| 0141 | 7433 | 217 | PRGH: | CALL |
| 0143 | B82E | 218 | | MOV |
| 0145 | FB | 219 | | MOV |
| 0146 | A0 | 220 | | MOV |
| 0147 | 18 | 221 | | INC |
| 0148 | FC | 222 | | MOV |
| 0149 | A0 | 223 | | MOV |
| 014A | 18 | 224 | | INC |
| 014B | 27 | 225 | | CLR |
| 014C | A0 | 226 | | MOV |
| 014D | 18 | 227 | | INC |
| 014E | A0 | 228 | | MOV |
| 014F | 7414 | 229 | PRGI: | CALL |
| 0151 | BA04 | 230 | | MOV |
| 0153 | B832 | 231 | | MOV |
| 0155 | B924 | 232 | | MOV |
| 0157 | 749C | 233 | PRGJ: | CALL |
| 0159 | EA57 | 234 | | DJNZ |
| 015B | BA02 | 235 | | MOV |
| 015D | B82C | 236 | | MOV |
| 015F | B920 | 237 | | MOV |
| 0161 | 749C | 238 | PRGK: | CALL |
| 0163 | EA61 | 239 | | DJNZ |
| 0165 | 7433 | 240 | PRGL: | CALL |
| 0167 | B832 | 241 | | MOV |
| 0169 | FB | 242 | | MOV |
| 016A | A0 | 243 | | MOV |
| 016B | 18 | 244 | | INC |
| 016C | FC | 245 | | MOV |
| 016D | A0 | 246 | | MOV |
| 016E | 18 | 247 | | INC |

-continued

ASM48 ATHRML.ASM DEBUG
ISIS-II MCS-48/UPI-41 MACRO ASSEMBLER, V2.0

| | | | |
|---|---|---|---|
| 016F | 27 | 248 | CLR |
| 0170 | A0 | 249 | MOV |
| 0171 | 18 | 250 | INC |
| 0172 | A0 | 251 | MOV |
| 0173 | 7414 | 252 PRGM: | CALL |
| 0175 | B820 | 253 | MOV |
| 0177 | B072 | 254 | MOV |
| 0179 | 18 | 255 | INC |
| 017A | B019 | 256 | MOV |
| 017C | BA04 | 257 | MOV |
| 017E | B82E | 258 | MOV |
| 0180 | B924 | 259 | MOV |
| 0182 | 749C | 260 PRGN: | CALL |
| 0184 | EA82 | 261 | DJNZ |
| 0186 | 7488 | 262 | CALL |
| 0188 | BA04 | 263 | MOV |
| 018A | B820 | 264 | MOV |
| 018C | B924 | 265 | MOV |
| 018E | 749C | 266 PRGO: | CALL |
| 0190 | EA8E | 267 | DJNZ |
| 0192 | BA04 | 268 | MOV |
| 0194 | B832 | 269 | MOV |
| 0196 | B920 | 270 | MOV |
| 0198 | 749C | 271 PRGP: | CALL |
| 019A | EA98 | 272 | DJNZ |
| 019C | 7474 | 273 | CALL |
| | | 274 | |
| 019E | 74C2 | 275 | CALL |
| 01A0 | B839 | 276 | MOV |
| 01A2 | 27 | 277 | CLR |
| 01A3 | A0 | 278 | MOV |
| 01A4 | 18 | 279 | INC |
| 01A5 | A0 | 280 | MOV |
| 01A6 | 18 | 281 | INC |
| 01A7 | A0 | 282 | MOV |
| 01A8 | 18 | 283 | INC |
| 01A9 | A0 | 284 | MOV |
| 01AA | BA02 | 285 | MOV |
| 01AC | B824 | 286 | MOV |
| 01AE | B92E | 287 | MOV |
| 01B0 | 749C | 288 PROGQ: | CALL |
| 01B2 | EAB0 | 289 | DJNZ |
| 01B4 | B820 | 290 | MOV |
| 01B6 | B050 | 291 | MOV |
| 01B8 | 18 | 292 | INC |
| 01B9 | B009 | 293 | MOV |
| 01BB | 27 | 294 | CLR |
| 01BC | 18 | 295 | INC |
| 01BD | A0 | 296 | MOV |
| 01BE | 18 | 297 | INC |
| 01BF | A0 | 298 | MOV |
| 01C0 | B826 | 299 | MOV |
| 01C2 | A0 | 300 | MOV |
| 01C3 | 18 | 301 | INC |
| 01C4 | A0 | 302 | MOV |
| 01C5 | 7474 | 303 | CALL |
| 01C7 | F6D7 | 304 | JC |
| 01C9 | 7414 | 305 | CALL |
| 01CB | BA02 | 306 | MOV |
| 01CD | B82E | 307 | MOV |
| 01CF | B924 | 308 | MOV |
| 01D1 | 749C | 309 PROGY: | CALL |
| 01D3 | EAD1 | 310 | DJNZ |
| 01D5 | 4415 | 311 | JMP |
| 01D7 | 7414 | 312 PROGX: | CALL |
| 01D9 | B824 | 313 | MOV |
| 01DB | B050 | 314 | MOV |
| 01DD | 18 | 315 | INC |
| 01DE | B009 | 316 | MOV |
| 01E0 | BA02 | 317 | MOV |
| 01E2 | B82E | 318 | MOV |
| 01E4 | B920 | 319 | MOV |
| 01E6 | 749C | 320 PROGT: | CALL |
| 01E8 | EAE6 | 321 | DJNZ |
| 01EA | 7474 | 322 | CALL |
| 01EC | 27 | 323 | CLR |
| 01ED | B825 | 324 | MOV |
| 01EF | 20 | 325 | XCH |
| 01F0 | C8 | 326 | DEC |
| 01F1 | 30 | 327 | XCHD |

-continued

ASM48 ATHRML.ASM DEBUG
ISIS-II MCS-48/UPI-41 MACRO ASSEMBLER, V2.0

| | | | | |
|---|---|---|---|---|
| 01F2 | 20 | 328 | | XCH |
| 01F3 | 47 | 329 | | SWAP |
| 01F4 | 20 | 330 | | XCH |
| 01F5 | BA02 | 331 | | MOV |
| 01F7 | B82E | 332 | | MOV |
| 01F9 | B920 | 333 | | MOV |
| 01FB | 749C | 334 | PROGU: | CALL |
| 01FD | EAFB | 335 | | DJNZ |
| 01FF | 7488 | 336 | | CALL |
| 0201 | BA02 | 337 | | MOV |
| 0203 | B820 | 338 | | MOV |
| 0205 | B92E | 339 | | MOV |
| 0207 | 749C | 340 | PROGV: | CALL |
| 0209 | EA07 | 341 | | DJNZ |
| 020B | BA02 | 342 | | MOV |
| 020D | B820 | 343 | | MOV |
| 020F | B924 | 344 | | MOV |
| 0211 | 749C | 345 | PROGW: | CALL |
| 0213 | EA11 | 346 | | DJNZ |
| 0215 | B839 | 347 | PROGS: | MOV |
| 0217 | B924 | 348 | | MOV |
| 0219 | F1 | 349 | | MOV |
| 021A | 30 | 350 | | XCHD |
| 021B | 47 | 351 | | SWAP |
| 021C | 18 | 352 | | INC |
| 021D | 30 | 353 | | XCHD |
| 021E | 19 | 354 | | INC |
| 021F | F1 | 355 | | MOV |
| 0220 | 18 | 356 | | INC |
| 0221 | 30 | 357 | | XCHD |
| 0222 | 47 | 358 | | SWAP |
| 0223 | 18 | 359 | | INC |
| 0224 | 30 | 360 | | XCHD |
| 0225 | F0 | 361 | LIMIT: | MOV |
| 0226 | C8 | 362 | | DEC |
| 0227 | C630 | 363 | | JZ |
| 0229 | F0 | 364 | | MOV |
| 022A | 03FD | 365 | | ADD |
| 022C | F637 | 366 | | JC |
| 022E | 4439 | 367 | | JMP |
| 0230 | F0 | 368 | LIMIT1: | MOV |
| 0231 | 03FC | 369 | | ADD |
| 0233 | F639 | 370 | | JC |
| 0234 | 6400 | 371 | | JMP |
| 0237 | 6400 | 372 | LIMIT2: | JMP |
| 0239 | 27 | 373 | LIMIT3: | CLR |
| 023A | B830 | 374 | | MOV |
| 023C | A0 | 375 | | MOV |
| 023D | 18 | 376 | | INC |
| 023E | A0 | 377 | | MOV |
| 023F | 7414 | 378 | | CALL |
| 0241 | BA04 | 379 | | MOV |
| 0243 | B82E | 380 | | MOV |
| 0245 | B924 | 381 | | MOV |
| 0247 | 749C | 382 | PROGR: | CALL |
| 0249 | EA47 | 383 | | DJNZ |
| 024B | B820 | 384 | | MOV |
| 024D | B020 | 385 | | MOV |
| 024F | 18 | 386 | | INC |
| 0250 | B003 | 387 | | MOV |
| 0252 | 7474 | 388 | | CALL |
| 0254 | 745C | 389 | | CALL |
| 0256 | B820 | 390 | | MOV |
| 0258 | B018 | 391 | | MOV |
| 025A | 27 | 392 | | CLR |
| 025B | 18 | 393 | | INC |
| 025C | A0 | 394 | | MOV |
| 025D | 18 | 395 | | INC |
| 025E | A0 | 396 | | MOV |
| 025F | 18 | 397 | | INC |
| 0260 | A0 | 398 | | MOV |
| 0261 | 7433 | 399 | | CALL |
| 0263 | B824 | 400 | | MOV |
| 0265 | FB | 401 | | MOV |
| 0266 | A0 | 402 | | MOV |
| 0267 | 18 | 403 | | INC |
| 0268 | FC | 404 | | MOV |
| 0269 | A0 | 405 | | MOV |
| 026A | B836 | 406 | | MOV |
| 026C | 27 | 407 | | CLR |

| | | | |
|---|---|---|---|
| 026D | A0 | 408 | MOV |
| 026E | 18 | 409 | INC |
| 026F | A0 | 410 | MOV |
| 0270 | 18 | 411 | INC |
| 0271 | A0 | 412 | MOV |
| 0272 | B836 | 413 | MOV |
| 0274 | B924 | 414 | MOV |
| 0276 | F1 | 415 | MOV |
| 0277 | 30 | 416 | XCHD |
| 0278 | 47 | 417 | SWAP |
| 0279 | 18 | 418 | INC |
| 027A | 30 | 419 | XCHD |
| 027B | 19 | 420 | INC |
| 027C | F1 | 421 | MOV |
| 027D | 18 | 422 | INC |
| 027E | 30 | 423 | XCHD |
| 027F | 04B1 | 424 | JMP |
| 0300 | | 425 | ORG |
| 0300 | B83D | 426 ERRRR: | MOV |
| 0302 | 23A0 | 427 | MOV |
| 0304 | A0 | 428 | MOV |
| 0305 | 18 | 429 | INC |
| 0306 | A0 | 430 | MOV |
| 0307 | 18 | 431 | INC |
| 0308 | 23F2 | 432 | MOV |
| 030A | A0 | 433 | MOV |
| 030B | 00 | 434 STP: | NOP |
| 030C | 640B | 435 | JMP |
| 0314 | | 436 | ORG |
| | | 437 | ; |
| | | 438 | ; |
| | | 439 | ; |
| 0314 | 27 | 440 CLEAR: | CLR |
| 0315 | BA08 | 441 | MOV |
| 0317 | B820 | 442 | MOV |
| 0319 | A0 | 443 CLR1: | MOV |
| 031A | 18 | 444 | INC |
| 031B | EA19 | 445 | DJNZ |
| 031D | 83 | 446 | RET |
| | | 447 | ; |
| | | 448 | ; |
| | | 449 | ; |
| | | 450 | ; |
| | | 451 | ; |
| | | 452 | ; |
| | | 453 | ; |
| | | 454 | ; |
| 031E | 7423 | 455 MULPLY: | CALL |
| 0320 | EB1E | 456 | DJNZ |
| 0322 | 83 | 457 | RET |
| 0323 | B820 | 458 MUL0: | MOV |
| 0325 | B924 | 459 | MOV |
| 0327 | BA04 | 460 | MOV |
| 0329 | 97 | 461 | CLR |
| 032A | F0 | 462 MUL1: | MOV |
| 032B | 71 | 463 | ADDC |
| 032C | 57 | 464 | DA |
| 032D | A0 | 465 | MOV |
| 032E | 18 | 466 | INC |
| 032F | 19 | 467 | INC |
| 0330 | EA2A | 468 | DJNZ |
| 0332 | 83 | 469 | RET |
| | | 470 | ; |
| | | 471 | ; |
| | | 472 | ; |
| | | 473 | ; |
| | | 474 | ; |
| | | 475 | ; |
| | | 476 | ; |
| | | 477 | ; |
| | | 478 | ; |
| | | 479 | ; |
| 0333 | 27 | 480 DIVIDE: | CLR |
| 0334 | AB | 481 | MOV |
| 0335 | AC | 482 | MOV |
| 0336 | BA04 | 483 DIV1: | MOV |
| 0338 | B824 | 484 | MOV |
| 033A | B920 | 485 | MOV |
| 033C | 97 | 486 | CLR |
| 033D | 2365 | 487 DIV2: | MOV |

|       |      |     |        |      |
|-------|------|-----|--------|------|
| Ø33F  | 71   | 488 |        | ADDC |
| Ø34Ø  | 37   | 489 |        | CPL  |
| Ø341  | 6Ø   | 49Ø |        | ADD  |
| Ø342  | 57   | 491 |        | DA   |
| Ø343  | A7   | 492 |        | CPL  |
|       |      | 493 |        |      |
|       |      | 494 |        |      |
| Ø344  | AØ   | 495 |        | MOV  |
| Ø345  | 18   | 496 |        | INC  |
| Ø346  | 19   | 497 |        | INC  |
| Ø347  | EA3D | 498 |        | DJNZ |
| Ø349  | F65B | 499 |        | JC   |
| Ø34B  | 2B   | 5ØØ |        | XCH  |
| Ø34C  | Ø3Ø1 | 5Ø1 |        | ADD  |
| Ø34E  | 57   | 5Ø2 |        | DA   |
| Ø34F  | 2B   | 5Ø3 |        | XCH  |
| Ø35Ø  | F654 | 5Ø4 |        | JC   |
| Ø352  | 6436 | 5Ø5 |        | JMP  |
| Ø354  | 2C   | 5Ø6 | DIV3:  | XCH  |
| Ø355  | Ø3Ø1 | 5Ø7 |        | ADD  |
| Ø357  | 57   | 5Ø8 |        | DA   |
| Ø358  | 2C   | 5Ø9 |        | XCH  |
| Ø359  | 6436 | 51Ø |        | JMP  |
| Ø35B  | 83   | 511 | DIV4:  | RET  |
|       |      | 512 |        | ;    |
|       |      | 513 |        | ;    |
|       |      | 514 |        | ;    |
|       |      | 515 |        | ;    |
|       |      | 516 |        | ;    |
| Ø35C  | 27   | 517 | SHIFT: | CLR  |
| Ø35D  | BAØ3 | 518 |        | MOV  |
| Ø35F  | B827 | 519 |        | MOV  |
| Ø361  | B926 | 52Ø |        | MOV  |
| Ø363  | 2Ø   | 521 | SHFT:  | XCH  |
| Ø364  | 47   | 522 |        | SWAP |
| Ø365  | 2Ø   | 523 |        | XCH  |
| Ø366  | 21   | 524 |        | XCH  |
| Ø367  | 47   | 525 |        | SWAP |
| Ø368  | 3Ø   | 526 |        | XCHD |
| Ø369  | 47   | 527 |        | SWAP |
| Ø36A  | 21   | 528 |        | XCH  |
| Ø36B  | C8   | 529 |        | DEC  |
| Ø36C  | C9   | 53Ø |        | DEC  |
| Ø36D  | EA63 | 531 |        | DJNZ |
| Ø36F  | 2Ø   | 532 |        | XCH  |
| Ø37Ø  | 47   | 533 |        | SWAP |
| Ø371  | 3Ø   | 534 |        | XCHD |
| Ø372  | 2Ø   | 535 |        | XCH  |
| Ø373  | 83   | 536 |        | RET  |
|       |      | 537 |        | ;    |
|       |      | 538 |        | ;    |
|       |      | 539 |        | ;    |
|       |      | 54Ø |        | ;    |
|       |      | 541 |        | ;    |
|       |      | 542 |        | ;    |
|       |      | 543 |        | ;    |
|       |      | 544 |        | ;    |
| Ø374  | BAØ4 | 545 | SUBBCD:| MOV  |
| Ø376  | B824 | 546 |        | MOV  |
| Ø378  | B92Ø | 547 |        | MOV  |
| Ø37A  | 97   | 548 |        | CLR  |
| Ø37B  | 2365 | 549 | SUBØ:  | MOV  |
| Ø37D  | 71   | 55Ø |        | ADDC |
| Ø37E  | 37   | 551 |        | CPL  |
| Ø37F  | 6Ø   | 552 |        | ADD  |
| Ø38Ø  | 57   | 553 |        | DA   |
| Ø381  | A7   | 554 |        | CPL  |
|       |      | 555 |        |      |
|       |      | 556 |        |      |
| Ø382  | AØ   | 557 |        | MOV  |
| Ø383  | 18   | 558 |        | INC  |
| Ø384  | 19   | 559 |        | INC  |
| Ø385  | EA7B | 56Ø |        | DJNZ |
| Ø387  | 83   | 561 |        | RET  |
|       |      | 562 |        | ;    |
|       |      | 563 |        | ;    |
|       |      | 564 |        | ;    |
|       |      | 565 |        | ;    |
|       |      | 566 |        | ;    |
|       |      | 567 |        | ;    |

-continued

ASM48 ATHRML.ASM DEBUG
ISIS-II MCS-48/UPI-41 MACRO ASSEMBLER, V2.0

| | | | | |
|---|---|---|---|---|
| | | 568 | | ; |
| 0388 | B820 | 569 | ADDBCD: | MOV |
| 038A | B924 | 570 | | MOV |
| 038C | BA04 | 571 | | MOV |
| 038E | 97 | 572 | | CLR |
| 038F | F0 | 573 | ADD1: | MOV |
| 0390 | 71 | 574 | | ADDC |
| 0391 | 57 | 575 | | DA |
| 0392 | A0 | 576 | | MOV |
| 0393 | 18 | 577 | | INC |
| 0394 | 19 | 578 | | INC |
| 0395 | EA8F | 579 | | DJNZ |
| 0397 | 83 | 580 | | RET |
| 0398 | 00 | 581 | | NOP |
| 0399 | 00 | 582 | | NOP |
| 039A | 00 | 583 | | NOP |
| 039B | 00 | 584 | | NOP |
| | | 585 | | ; |
| | | 586 | | ; |
| | | 587 | | ; |
| | | 588 | | ; |
| 039C | F0 | 589 | MOVE: | MOV |
| 039D | A1 | 590 | | MOV |
| 039E | 18 | 591 | | INC |
| 039F | 19 | 592 | | INC |
| 03A0 | 83 | 593 | | RET |
| 03A1 | 00 | 594 | | NOP |
| 03A2 | 00 | 595 | | NOP |
| 03A3 | 00 | 596 | | NOP |
| | | 597 | | ; |
| 03A4 | D5 | 598 | DISPLY: | SEL |
| 03A5 | AC | 599 | | MOV |
| 03A6 | B5 | 600 | | CPL |
| 03A7 | B83D | 601 | | MOV |
| 03A9 | F0 | 602 | | MOV |
| 03AA | 76AD | 603 | | JF1 |
| 03AC | 37 | 604 | | CPL |
| 03AD | 39 | 605 | DOUT1: | OUTL |
| 03AE | 18 | 606 | | INC |
| 03AF | F0 | 607 | | MOV |
| 03B0 | 76B3 | 608 | | JF1 |
| 03B2 | 37 | 609 | | CPL |
| 03B3 | 3A | 610 | DOUT2: | OUTL |
| 03B4 | 18 | 611 | | INC |
| 03B5 | F0 | 612 | | MOV |
| 03B6 | 76B9 | 613 | | JF1 |
| 03B8 | 37 | 614 | | CPL |
| 03B9 | 02 | 615 | DOUT3: | OUTL |
| 03BA | 2380 | 616 | | MOV |
| 03BC | 62 | 617 | | MOV |
| 03BD | FC | 618 | | MOV |
| 03BE | C5 | 619 | | SEL |
| 03BF | 93 | 620 | | RETR |
| 03C0 | 00 | 621 | | NOP |
| 03C1 | 00 | 622 | | NOP |
| | | 623 | | ; |
| | | 624 | | ; |
| | | 625 | | ; |
| | | 626 | | ; |
| | | 627 | | ; |
| 03C2 | BA03 | 628 | DVTWO: | MOV |
| 03C4 | B820 | 629 | | MOV |
| 03C6 | 2302 | 630 | | MOV |
| 03C8 | A0 | 631 | | MOV |
| 03C9 | 27 | 632 | | CLR |
| 03CA | 18 | 633 | DVTWO1: | INC |
| 03CB | A0 | 634 | | MOV |
| 03CC | EACA | 635 | | DJNZ |
| 03CE | 7433 | 636 | | CALL |
| 03D0 | B824 | 637 | | MOV |
| | | 638 | | |
| 03D2 | FB | 639 | | MOV |
| 03D3 | A0 | 640 | | MOV |
| 03D4 | 18 | 641 | | INC |
| 03D5 | FC | 642 | | MOV |
| 03D6 | A0 | 643 | | MOV |
| 03D7 | 83 | 644 | | RET |
| 03D8 | 00 | 645 | | NOP |
| 03F0 | | 646 | | ORG |
| 03F0 | 7E | 647 | | DB |

-continued

ASM48 ATHRML.ASM DEBUG
ISIS-II MCS-48/UPI-41 MACRO ASSEMBLER, V2.0

| | | | |
|---|---|---|---|
| 03F1 | 0C | 648 | DB |
| 03F2 | B6 | 649 | DB |
| 03F3 | 9E | 650 | DB |
| 03F4 | CC | 651 | DB |
| 03F5 | DA | 652 | DB |
| 03F6 | FA | 653 | DB |
| 03F7 | 0E | 654 | DB |
| 03F8 | FE | 655 | DB |
| 03F9 | DE | 656 | DB |
| 03FA | A0 | 657 | DB |

| LOC | OBJ | SEQ | SOURCE STATEMENT | |
|---|---|---|---|---|
| 03FB | F2 | 658 | DB | 0F2H |
| 03FC | 00 | 659 | DB | 0H |
| 03FD | 00 | 660 | DB | 0H |
| 03FE | 00 | 661 | DB | 0H |
| 03FF | 00 | 662 | DB | 0H |
| 0000 |  | 663 | END | START |

USER SYMBOLS

| | | | | | | | | | |
|---|---|---|---|---|---|---|---|---|---|
| ADD1 | 038F | ADDBCD | 0388 | CLEAR | 0314 | CLR1 | 0319 | DISPLY | 03A4 |
| DIV4 | 035B | DIVIDE | 0333 | DOUT1 | 03AD | DOUT2 | 03B3 | DOUT3 | 03B9 |
| ERR1 | 0079 | ERRDET | 0069 | ERRRR | 0300 | FPRG | 00EF | FTMP | 00EA |
| LIMIT1 | 0230 | LIMIT2 | 0237 | LIMIT3 | 0239 | MOVE | 039C | MUL0 | 0323 |
| PRGB | 010B | PRGC | 0117 | PRGD | 0127 | PRGE | 012B | PRGF | 0133 |
| PRGJ | 0157 | PRGK | 0161 | PRGL | 0165 | PRGM | 0173 | PRGN | 0182 |
| PROG0 | 0011 | PROG1 | 0084 | PROG2 | 008E | PROG3 | 00A6 | PROGQ | 01B0 |
| PROGT | 01E6 | PROGU | 01FB | PROGV | 0207 | PROGW | 0211 | PROGX | 01D7 |
| REFPH1 | 002A | REFPH2 | 002E | REFPH3 | 003D | REFPH4 | 0026 | REFPHX | 0014 |
| START | 0000 | STP | 030B | SUB0 | 037B | SUBBCD | 0374 | TMP1 | 00BB |
| TMPPH1 | 005B | TMPSEL | 00B1 | | | | | | |
| | | | | | | | | | |
| DIV1 | 0336 | DIV2 | 033D | DIV3 | 0354 | | | | |
| DVTWO | 03C2 | DVTWO1 | 03CA | ERR0 | 006A | | | | |
| GODISP | 0007 | HAFRT | 009A | LIMIT | 0225 | | | | |
| MUL1 | 032A | MULPLY | 031E | PRGA | 00FB | | | | |
| PRGG | 013D | PRGH | 0141 | PRGI | 014F | | | | |
| PRGO | 018E | PRGP | 0198 | PROG | 0009 | | | | |
| PROGR | 0247 | PROGRM | 007B | PROGS | 0215 | | | | |
| PROGY | 01D1 | REFPH | 001F | REFPH0 | 0023 | | | | |
| REFPHY | 0018 | SHFT | 0363 | SHIFT | 035C | | | | |
| TMP2 | 00D1 | TMP3 | 00D3 | TMPPH | 004C | | | | |

ASSEMBLY COMPLETE, NO ERRORS

I claim:

1. A patient temperature monitoring system comprising a plurality of transmitters, one associated with each patient to be monitored, and a receiver, each transmitter comprising a thermistor for thermal contact with a portion of the body of a patient whose temperature is to be measured, reference resistence means, means coupled to said thermistor and said reference resistence means for providing a high frequency output signal having a duty cycle proportional to a ratio of value of resistance of said thermistor relative to said reference resistence means, an electrical power supply coupled to said means for providing said output signal, a normally open magnetically actuable switch interposed between said electrical power supply and said means for providing said output signal, a transmitter case encompassing said electrical power supply, said magnetically actuable switch and said means for providing said output signal, said receiver comprising:

demodulating means responsive to said high frequency transmitter output signal for providing an envelope signal of duration proportional to the duration of said transmitter duty cycle output, microprocessor means coupled to receive an input from said demodulating means to calculate patient temperature in both Fahrenheit and Centigrade conventions, display means coupled to said microprocessor output and including manually actuable selection means to alternatively display patient temperature in degrees Fahrenheit and degrees Centigrade an to indicate the convention displayed, magnetic switch actuating means for selectively and momentarily closing said magnetically actuable switch by means of magnetic force in a selected, proximately located transmitter, to the exclusion of magnetically actuable switches in other transmitters, whereby said magnetically actuable switches in said plurality of transmitters are normally open and said transmitters exert no power drain on their respective electrical supplies unless said magnetically actuable switch in a selected transmitter is closed by said magnetic switch actuating means in said receiver.

2. A patient temperature monitoring system according to claim 1 wherein said receiver has a portable case housing said demodulating means, said microprocessor and said display means, and an antenna extends from said case and is connected to said demodulating means, and said magnetic switch actuating means includes a magnet carried on said antenna remote from said case, and said electrical power supply in said transmitter is a d.c. electrical power supply and said magnetically actuated switch is a reed switch connected in a main power supply line to said means for providing a high frequency output signal, and said reed switch is accessable to the magnetic field of said magnet, whereby said antenna may be moved to position said magnet proximate to said reed switch to close said reed switch to provide power to said transmitter, and said transmitter exerts no power drain on its electrical power supply unless said reed switch is closed.

3. A patient temperature monitoring system according to claim 1 wherein said receiver has a portable case housing said demodulating means, said microprocessor and said display means, and said magnetic switch actuating means includes an antenna that extends from said case and is connected to said modulating means, and said magnetic switch actuating means comprises a magnet carried on said antenna remote from said case, and said magnetically actuable switch in said transmitter is a reed switch positioned at the inner surface of said transmitter case, whereby said reed switch is accessable to the magnetic field of said magnet when said receiver antenna is moved to position said magnet proximate to said reed switch outside of said transmitter case, whereupon said magnet closes said reed switch to power said transmitter and said transmitter exerts no power drain on its electrical power supply unless said reed switch is closed.

* * * * *